(12) United States Patent
Chang

(10) Patent No.: US 7,786,274 B2
(45) Date of Patent: *Aug. 31, 2010

(54) ANTI-IL-20 ANTIBODY AND ITS USE IN TREATING IL-20 ASSOCIATED INFLAMMATORY DISEASES

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/238,760

(22) Filed: Sep. 26, 2008

(65) Prior Publication Data

US 2009/0048432 A1 Feb. 19, 2009

Related U.S. Application Data

(62) Division of application No. 11/763,812, filed on Jun. 15, 2007, now Pat. No. 7,611,705.

(51) Int. Cl.
*C07K 16/00* (2006.01)
(52) U.S. Cl. ............... 530/388.23; 530/387.1; 530/387.3; 530/351
(58) Field of Classification Search ............. None
See application file for complete search history.

(56) References Cited

U.S. PATENT DOCUMENTS

| 7,122,632 | B2 | 10/2006 | Foster et al. |
| 7,435,800 | B2 * | 10/2008 | Chang ............ 530/388.23 |
| 2005/0003475 | A1 | 1/2005 | Foster et al. |
| 2005/0136004 | A1 | 6/2005 | Xu et al. |
| 2006/0142550 | A1 | 6/2006 | Chang |
| 2006/0177447 | A1 | 8/2006 | Xu |
| 2006/0269551 | A1 | 11/2006 | Thompson et al. |

OTHER PUBLICATIONS

Hsu Y.H. et al., "Function of Interleukin-20 as a proinflammatory molecule in rheumatoid and experimental arthritis", Arthritis and Rheumatism, vol. 54(9), pp. 2722-2733 (Sep. 2006).
Hsieh M.Y. et al., "Interleukin-20 promotes angiogenesis in a direct and indirect manner", Genes and Immunity, vol. 7(3), pp. 234-242 (Apr. 2006).
Wei C.C. et al., "IL-20: Biological functions and clinical implications", Journal of Biomedical Science, vol. 13(5), pp. 601-612 (May 16, 2006).
Sabat R. et al., "IL-19 and IL-20: Two novel cytokines with importance in inflammatory diseases", Expert Opinion on Therapeutic Targets, vol. 11(5), pp. 601-612 (May 2007).
Wei C.C. et al., "Detection of IL-20 and its receptors on psoriatic skin", Clinical Immunology, vol. 117(1), pp. 65-72 (Oct. 2005).

* cited by examiner

*Primary Examiner*—Dong Jiang
(74) *Attorney, Agent, or Firm*—Occhiuti Rohlicek & Tsao LLP

(57) ABSTRACT

This invention features an antibody specifically binding to human IL-20 (e.g., mAb 7E and a equivalent thereof) and its use in treating an IL-20 associated inflammatory disease, such as atherosclerosis, RA, psoriasis, psoriatic arthritis, bacteria-induced gastric ulcer, and acute renal failure.

4 Claims, No Drawings

ANTI-IL-20 ANTIBODY AND ITS USE IN TREATING IL-20 ASSOCIATED INFLAMMATORY DISEASES

RELATED APPLICATIONS

This application is a divisional application claiming priority to U.S. application Ser. No. 11/763,812, filed Jun. 15, 2007, the contents of which are incorporated herein in their entirety.

BACKGROUND

Inflammation refers to a localized, protective response to trauma or microbial invasion to remove the injurious stimuli and initiate the healing process for the tissue. Deficiencies of inflammation render a patient vulnerable to pathogen infections. Excessive inflammation caused by abnormal recognition of host tissues as foreign, on the other hand, may lead to various inflammatory diseases, e.g., atherosclerosis and rheumatoid arthritis (RA).

Atherosclerosis is a chronic inflammatory disease in which fatty materials aggregate along the walls of arteries to form atherosclerotic plaques. It is suggested that foam cell macrophages play an important role in the progress of this disease. They secret various types of cytokines and chemokines, which direct and amplify local immune responses. Several chemokines and cytokines have been found to be expressed at elevated levels at atherosclerotic lesions, suggesting their involvement in disease development.

RA is the most common form of inflammatory arthritis characterized by intense inflammation in synovial joints, causing infiltration of mononuclear phagocytes, lymphocyts, and neutrophils into synovial membranes. Recent studies show that cytokines and chemokines, such as tumor necrosis factor α (TNFα), interleukin-1β (IL-1β), IL-6, and IL-8, are substantially involved in disease progression IL-20 is a newly discovered member of the IL-10 family. Other members of this family have been found to be crucial in the development of many inflammatory diseases, e.g., RA. IL-20 selectively increases levels of multipotential hematopoietic progenitors. It also induces the proliferation of keratinocytes, which in turn over-express proinflammatory genes.

SUMMARY

In one aspect, this invention features an antibody specifically binding to human IL-20, i.e., mAb 7E, and its functional equivalents. Examples of a functional equivalents of mAb 7E include antibodies that have the same heavy and light chain variable regions ($V_H$ and $V_L$) as mAb 7E, such as fragments of mAb 7E (e.g., Fab, $F(ab')_2$), single-chain variable fragment (scFv) of mAb 7E, and chimeric antibody made from mAb 7E. Other examples include humanized antibodies of mAb 7E.

In another aspect, this invention features a method of treating IL-20 associated inflammatory diseases by administering an effective amount of an anti-IL-20 antibody, e.g., mAb 7E or its functional equivalents. The IL-20 associated inflammatory disease includes but is not limited to atherosclerosis, rheumatoid arthritis, psoriasis, psoriatic arthritis, acute renal failure, and gastric ulcer (e.g., bacteria-induced gastric ulcer). The antibody can be administered intravenously or directed to the site where inflammation occurs.

Also within the scope of this invention is a method of treating tumor, such as solid tumor, by administering an effective amount of an anti-IL-20 antibody, e.g., mAb 7E or a functional equivalent thereof, to a patient who needs the treatment.

MAb 7E and its functional equivalents also can be used in the manufacture of medicaments for treating IL-20 associated inflammation.

The details of one or more embodiments of the invention are set forth in the description below. Other features, objects, and advantages of the invention will be apparent from the description, and from the claims.

DETAILED DESCRIPTION

Within the scope of this invention are a monoclonal anti-IL-20 antibody 7E (mAb 7E) and its functional equivalents. The term "functional equivalent" refers to an antibody that (1) specifically binds to human IL-20, and (2) contains a $V_H$ region at least 70% (e.g., 80%, 90%, or 95%) identical to that of mAb 7E (SEQ ID NO:20) and a $V_L$ region at least 70% (e.g., 80%, 90%, or 95%) identical to that of mAb 7E (SEQ ID NO:21).

MAb 7E can be made according to the method described below. The amino acid sequences/cDNA sequences of its heavy and light chains are shown below.

Nucleotide sequence (SEQ ID NO: 1) and amino acid sequence (SEQ ID NO: 2) of mAb 7E heavy chain

| atg | tac | ttg | gga | ctg | aac | tat | gta | ttc | ata | gtt | ttt | ctc | tta | aat | |
|-----|-----|-----|-----|-----|-----|-----|-----|-----|-----|-----|-----|-----|-----|-----|---|
| M | Y | L | G | L | N | Y | V | F | I | V | F | L | L | N | 15 |

| ggt | gtc | cag | agt | gaa | ttg | aag | ctt | gag | gag | tct | gga | gga | ggc | ttg | |
|-----|-----|-----|-----|-----|-----|-----|-----|-----|-----|-----|-----|-----|-----|-----|---|
| G | V | Q | S | E | L | K | L | E | E | S | G | G | G | L | 30 |

| gtg | cag | cct | gga | gga | tcc | atg | aaa | ctc | tct | tgt | gct | gcc | tct | gga | |
|-----|-----|-----|-----|-----|-----|-----|-----|-----|-----|-----|-----|-----|-----|-----|---|
| V | Q | P | G | G | S | M | K | L | S | C | A | A | S | G | 45 |

| ttc | act | ttt | agt | gac | gcc | tgg | atg | gac | tgg | gtc | cgc | cag | tct | cca | |
|-----|-----|-----|-----|-----|-----|-----|-----|-----|-----|-----|-----|-----|-----|-----|---|
| F | T | F | S | D | A | W | M | D | W | V | R | Q | S | P | 60 |

| gag | aag | ggg | ctt | gag | tgg | att | gct | gaa | att | aga | agc | aaa | gct | aat | |
|-----|-----|-----|-----|-----|-----|-----|-----|-----|-----|-----|-----|-----|-----|-----|---|
| E | K | G | L | E | W | I | A | E | I | R | S | K | A | N | 75 |

| aat | tat | gca | aca | tac | ttt | gct | gag | tct | gtg | aaa | ggg | agg | ttc | acc | |
|-----|-----|-----|-----|-----|-----|-----|-----|-----|-----|-----|-----|-----|-----|-----|---|
| N | Y | A | T | Y | F | A | E | S | V | K | G | R | F | T | 90 |

Nucleotide sequence (SEQ ID NO: 1) and amino acid sequence
(SEQ ID NO: 2) of mAb 7E heavy chain

```
atc tca aga gat gat tcc aaa agt ggt gtc tac ctg caa atg aac
 I   S   R   D   D   S   K   S   G   V   Y   L   Q   M   N    105 aac tta aga gct gag gac act ggc att tat ttc tgt acc aag tta
 N   L   R   A   E   D   T   G   I   Y   F   C   T   K   L    120 tca cta cgt tac tgg ttc ttc gat gtc tgg ggc gca ggg acc acg
 S   L   R   Y   W   F   F   D   V   W   G   A   G   T   T    135 gtc acc gtc tcc tca gcc aaa acg aca ccc cca tct gtc tat cca
 V   T   V   S   S   A   K   T   T   P   P   S   V   Y   P    150 ctg gcc cct gga tct gct gcc caa act aac tcc atg gtg acc ctg
 L   A   P   G   S   A   A   Q   T   N   S   M   V   T   L    175 gga tgc ctg gtc aag ggc tat ttc cct gag cca gtg aca gtg acc
 G   C   L   V   K   G   Y   F   P   E   P   V   T   V   T    190 tgg aac tct gga tcc ctg tcc agc ggt gtg cac acc ttc cca gct
 W   N   S   G   S   L   S   S   G   V   H   T   F   P   A    205 gtc ctg cag tct gac ctc tac act ctg agc agc tca gtg act gtc
 V   L   Q   S   D   L   Y   T   L   S   S   S   V   T   V    230 ccc tcc agc acc tgg ccc agc gag acc gtc acc tgc aac gtt gcc
 P   S   S   T   W   P   S   E   T   V   T   C   N   V   A    245 cac ccg gcc agc agc acc aag gtg gac aag aaa att gtg ccc agg
 H   P   A   S   S   T   K   V   D   K   K   I   V   P   R    270 gat tgt ggt tgt aag cct tgc ata tgt aca gtc cca gaa gta tca
 D   C   G   C   K   P   C   I   C   T   V   P   E   V   S    285 tct gtc ttc atc ttc ccc cca aag ccc aag gat gtg ctc acc att
 S   V   F   I   F   P   P   K   P   K   D   V   L   T   I    300 act ctg act cct aag gtc acg tgt gtt gtg gta gac atc agc aag
 T   L   T   P   K   V   T   C   V   V   V   D   I   S   K    315 gat gat ccc gag gtc cag ttc agc tgg ttt gta gat gat gtg gag
 D   D   P   E   V   Q   F   S   W   F   V   D   D   V   E    330 gtg cac aca gct cag acg caa ccc cgg gag gag cag ttc aac agc
 V   H   T   A   Q   T   Q   P   R   E   E   Q   F   N   S    345 act ttc cgc tca gtc agt gaa ctt ccc atc atg cac cag gac tgg
 T   F   R   S   V   S   E   L   P   I   M   H   Q   D   W    360 ctc aat ggc aag gag ttc aaa tgc agg gtc aac agt gca gct ttc
 L   N   G   K   E   F   K   C   R   V   N   S   A   A   F    375 cct gcc ccc atc gag aaa acc atc tcc aaa acc aaa ggc aga ccg
 P   A   P   I   E   K   T   I   S   K   T   K   G   R   P    390 aag gct cca cag gtg tac acc att cca cct ccc aag gag cag atg
 K   A   P   Q   V   Y   T   I   P   P   P   K   E   Q   M    405 gcc aag gat aaa gtc agt ctg acc tgc atg ata aca gac ttc ttc
 A   K   D   K   V   S   L   T   C   M   I   T   D   F   F    420 cct gaa gac att act gtg gag tgg cag tgg aat ggg cag cca gcg
 P   E   D   I   T   V   E   W   Q   W   N   G   Q   P   A    435 gag aac tac aag aac act cag ccc atc atg gac aca gat ggc tct
 E   N   Y   K   N   T   Q   P   I   M   D   T   D   G   S    450 tac ttc gtc tac agc aag ctc aat gtg cag aag agc aac tgg gag
 Y   F   V   Y   S   K   L   N   V   Q   K   S   N   W   E    465 gca gga aat act ttc acc tgc tct gtg tta cat gag ggc ctg cac
 A   G   N   T   F   T   C   S   V   L   H   E   G   L   H    480 aac cac cat act gag aag agc ctc tcc cac tct cct ggt aaa TGA
 N   H   H   T   E   K   S   L   S   H   S   P   G   K   -    494
```

The highlighted region refers to the variable region of mAb 7E heavy chain (DNA sequence SEQ ID NO:3; Protein sequence SEQ ID NO:20)

can be a single-chain antibody including the $V_H$ and $V_L$ of mAb 7E covalently fused via a linker, e.g., a peptide linker. In addition, it can be a mouse-human chimeric antibody that Nucleotide sequence (SEQ ID NO: 4) and amino acid sequence (SEQ ID NO: 5) of mAb 7E light chain

```
atg atg agt cct gcc cag ttc ctg ttt ctg tta gtg ctc tgg att
 M   M   S   P   A   Q   F   L   F   L   L   V   L   W   I     15 cgg gaa acc aac ggt gat ttt gtg atg acc cag act cca ctc act
 R   E   T   N   G   D   F   V   M   T   Q   T   P   L   T     30 ttg tcg gtt acc att gga caa cca gcc tcc atc tct tgc aag tca
 L   S   V   T   I   G   Q   P   A   S   I   S   C   K   S     45 agt cag agc ctc ttg gat agt gat gga aag aca tat ttg aat tgg
 S   Q   S   L   L   D   S   D   G   K   T   Y   L   N   W     60 ttg tta cag agg cca ggc cag tct cca aag cac ctc atc tat ctg
 L   L   Q   R   P   G   Q   S   P   K   H   L   I   Y   L     75 gtg tct aaa ctg gac tct gga gtc cct gac agg ttc act ggc agt
 V   S   K   L   D   S   G   V   P   D   R   F   T   G   S     90 gga tca ggg acc gat ttc aca ctg aga atc agc aga gtg gag gct
 G   S   G   T   D   F   T   L   R   I   S   R   V   E   A    105 gag gat ttg gga gtt tat tat tgc tgg caa agt aca cat ttt ccg
 E   D   L   G   V   Y   Y   C   W   Q   S   T   H   F   P    120 tgg acg ttc ggt gga ggc acc aag ctg gaa atc aaa cgg gct gat
 W   T   F   G   G   G   T   K   L   E   I   K   R   A   D    135 gct gca cca act gta tcc atc ttc cca cca tcc agt gag cag tta
 A   A   P   T   V   S   I   F   P   P   S   S   E   Q   L    150 aca tct gga ggt gcc tca gtc gtg tgc ttc ttg aac aac ttc tac
 T   S   G   G   A   S   V   V   C   F   L   N   N   F   Y    175 aag tgg aag att gat ggc agt gaa cga caa aat ggc gtc ctg aac
 P   K   D   I   N   V   K   W   K   I   D   G   S   E   R    180 agt tgg act gat cag ccc aaa gac atc aat gtc gac agc aaa gac
 Q   N   G   V   L   N   S   W   T   D   Q   D   S   K   D    195 agc acc tac agc atg agc agc acc ctc acg ttg acc aag gac gag
 S   T   Y   S   M   S   S   T   L   T   L   T   K   D   E    210 tat gaa cga cat aac agc tat acc tgt gag gcc act cac aag aca
 Y   E   R   H   N   S   Y   T   C   E   A   T   H   K   T    225 tca act tca ccc att gtc aag agc ttc aac agg aat gag tgt tag
 S   T   S   P   I   V   K   S   F   N   R   N   E   C   -    239
```

The highlighted region refers to the variable region of mAb 7E light chain (DNA sequence SEQ ID NO:6; Protein sequence SEQ ID NO:21)

As used herein, "percent homology" of two amino acid sequences is determined using the algorism described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorism is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alighments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

A functional equivalent of mAb 7E can be its fragment generated by enzyme digestion, e.g., Fab or F(ab')$_2$. It also contains the $V_H$ and $V_L$ of mAb 7E, which are respectively linked with the constant regions of the heavy and light chains of a human IgG. Alternatively, the functional equivalent can be a humanized antibody. The term "humanized antibody" refers to a non-human antibody, in which the frame regions (FRs) of its $V_H$ and $V_L$ are replaced with FRs of a human antibody. Further, the mAb 7E functional equivalent can be generated by introducing mutations in the FRs of either $V_H$ or $V_L$. It is well known that complementarity-determining regions (CDRs) of an antibody determine its specificity. Accordingly, mutations in FRs normally would not affect antibody specificity. The CDRs and FRs of an antibody can be determined based on the amino acid sequences of its $V_H$ and $V_L$. See www.bioinf.org.uk/abs. The binding-specificity of the functional equivalents described herein can be examined using methods known in the art, e.g., ELISA or western-blot analysis.

MAb 7E and its functional equivalents can be prepared either by purifying the antibody secreted from the hybridoma cells described above, or by genetic engineering.

This invention also features a method of treating an IL-20 associated inflammatory disease using an effective amount of anti-IL-20 antibody, e.g., mAb 7E or its functional equivalents.

The term "IL-20 associated inflammatory disease" refers to an inflammatory disease in which IL-20 plays a role in either its initiation or progression. IL-20 has been found to be involved in the development of inflammatory diseases such as atherosclerosis and rheumatoid arthritis. See Chen et al., *Arteriosclerosis, Thrombosis, and Vascular Biology*, 26:2090-2095, 2006; and Hsu et al., *Arthritis & Rheumatism*, 54(9):2722-2733, 2006. In addition, IL-20 upregulates IL-8, a proinflammatory factor that plays important roles in many inflammatory diseases, e.g., psoriasis, septic shock, and inflammatory bowel disease. See U.S. patent application 2006/0269551. IL-20 has also been found to be involved in acute renal failure and bacteria-induced gastric ulcer. Thus, antibodies that inhibit IL-20 function are effective in treating IL-20 associated inflammatory diseases.

A subject suffering from an IL-20 associated inflammatory disease refers to a subject (e.g., a human patient) who has at least one symptom of the disease, e.g., redness, swelling, or pain at the site where inflammation occurs. For example, a patient suffering from atherosclerosis refers to a patient who has at least one atheromatous plaque (a symptom of atherosclerosis), which can be detected by routine medical procedures. Such a patient can exhibit insufficient blood supply to an organ due to plaque ruptures or artery stenosis. He and she can have symptoms such as chest pain if an artery to the heart is involved or leg pain when a leg artery is involved. In another example, a patient suffering from RA has inflammation in synovial joints, resulting in redness, swelling, pain, or stiffness in the joints, and infiltration of immune cells into synovial membranes. In some RA patients, chronic inflammation leads to the destruction of the cartilage, bone, and ligaments, causing deformity of the joints. Patients having severe RA can lose function of their joints.

A subject having a risk of an IL-20 associated inflammatory disease refers to a subject who bears one or more risk factors of that disease, such as genetic background, family history, and life habits (e.g., diet, or smoking). A patient who is "at risk for atherosclerosis" bears one or more risk factors for atherosclerosis, e.g., personal or family history of heart diseases, high-fat diet, smoking, obesity, high blood pressure, and a high blood cholesterol level. A patient having a risk for RA may have a smoking habit or a family history of autoimmune diseases.

The term "treating an inflammatory disease" used herein, unless otherwise indicated, means relieving the symptoms of the disease, reversing, ameliorating, or inhibiting the progress of the inflammation associated with the disease.

The term "effective amount" as used herein, refers to an amount or concentration of an agent utilized for a period of time (including acute or chronic administration and periodic or continuous administration) that is effective within the context of its administration for causing an intended effect or physiological outcome. An effective amount of an anti-IL-20 antibody for use in this invention include, for example, amounts that are effective for preventing or inhibiting an IL-20 associated inflammation in a subject, or for relieving or ameliorating the symptoms of such inflammation, e.g., redness, swelling, pain, and loss of function of an organ where inflammation occurs.

The anti-IL-20 antibody described herein can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

Conventional methods, known to those of ordinary skill in the art of medicine, can be used to administer the anti-IL-20-antibody-containing pharmaceutical composition to the subject, depending upon the type of inflammatory disease to be treated or the site of the inflammation associated with the disease. For treating atherosclerosis, the composition can be administered via intravenous injection. For treating rheumatoid arthritis, the antibody-containing composition can be delivered directly to synovial joints via injection. This composition can also be administered via other conventional routes, e.g., subcutaneous. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Upregulation of Both IL-20 and Its Receptors in Atherosclerosis Lesions of apoE−/− Mice C57BL/6 apoE$^{-/-}$ (from The Jackson Laboratory, Bar Harbor, Me.) mice were fed with a regular chow diet or an atherogenic diet containing 0.15% of cholesterol. At week 24, hearts and ascending aortas of the mice were excised, fixed in formaldehyde, and serial 10-μm-thick cryosections were cut from the aortic arch to the ventricles.

The cryosections were then fixed in 4% paraformaldehyde on a slide and immersed in antibody diluent with background-reducing components (DakoCytomation, Carpinteria, Calif.) for 60 minutes to suppress nonspecific immunoglobulin staining. The slides were soaked in 90 ml of methanol and 10 ml of 30% $H_2O_2$ for 10 minutes at room temperature to block endogenous peroxidases, washed with PBS, and then incubated with anti-hIL-20R2 rabbit-polyclonal antibody in blocking reagent at 4° C. overnight. The slides were then treated consecutively with HRP-conjugated goat anti-rabbit IgG (Biolegend, San Diego, Calif.) and incubated for 2 hours at room temperature. Slides were incubated with the diaminobenzidine DAB substrate kit (Vector Laboratories, Burlingame, Calif.) and counterstained with Mayer's hematoxylin (Thermoshandon, Pittsburgh, Pa.). Negative control, which was not incubated with primary antibody, was performed simultaneously.

To stain IL-20R1, one of the IL-20 receptors, primary antibody (R&D Systems) was diluted to 1:150 using a staining kit (Vector M.O.M. Peroxidase Kit PK-2200; Vector Laboratories) and Vectastain Elite ABC reagent (included in the M.O.M. kit) according to the manufacturer's protocol. Mouse IgG1 isotype (clone 1171 1; R&D Systems) was used as a negative control. HRP-conjugated goat anti-mouse IgG (Biolegend) was used as the secondary antibody to detect the signal of the primary antibody bound to the tissue.

To stain mouse IL-20, primary antibody (clone 176005; R&D Systems) was diluted to 1:200 and detected with biotin-labeled rat anti-mouse IgG secondary antibody and ABC reagent.

IL-20 was found to be upregulated in the atherosclerosis plaques of apoE$^{-/-}$ mice compared with normal C57BL/6 mice. IL-20 was also detected in Mac-3-rich (foam cells/macrophages) area. Increased immunoreactivity was also detected for both IL-20R1 and IL-20 R2 in the atherosclerosis plaques, the endothelium, and the adventitia of the aortic arches of apoE$^{-/-}$ mice, compared to the wild-type mice.

These results indicate that the levels of both IL-20 and IL-20 receptors were increased in atherosclerosis plaques and were markedly upregulated in the endothelium of atherosclerotic aortas. It is likely that foam cells/macrophages are the major producer of IL-20 in the plaques.

Upregulation of Both IL-20 and its Receptors in Human Atherosclerotic Artery

The levels of IL-20 and its receptors were also examined in human atherosclerotic artery following the method described above. Briefly, surgical femoral arterial samples from atherosclerotic patients were fixed in paraffin and sliced to 10-µm-thick sections. In these sections, pronounced thickening occurred in the intima and media, both of which exhibited extensive angiogenesis.

IL-20 was detected in endothelial cells lining the microvessels and macrophage-derived foam cells that exhibited positive staining of CD68. Both IL-20R1 and IL-20R2 were detected primarily in endothelial cells of the vasa vasorum. By contrast, IL-20 was not detected in normal aorta sections and only a low level of its receptors was detected in the endothelium of normal aorta sections.

To determine whether IL-20 was induced by existing inflammatory stimuli in the atherosclerotic lesions, reverse transcription polymerase chain reactions (RT-PCRs) were performed to examine IL-20 mRNA levels in Oxidized LDL (OxLDL)-treated human peripheral monocytes.

Human native LDL was isolated from human blood plasma using discontinuous centrifugation. LDL was oxidized by exposing it to $CuSO_4$ (5-µM free $Cu^{2+}$) in PBS at 37° C. for 8 hours. OxLDL was kept in 50 mM Tris-HCl, 0.15 M NaCl, and 2 mM EDTA at pH7.4 and was used within 10 days after preparation. Human monocytes were isolated from peripheral blood samples of healthy donors and cultured in serum-free RPMI. RAW264.7, a mouse macrophage cell line, was cultured in DMEM medium with 10% FBS. Human monocytes ($1 \times 10^6$ cells) or RAW264.7 ($1 \times 10^6$ cells) cells were incubated with OxLDL (1, 10, or 100 µg/ml) for 6 hours. Total RNAs were purified from these cells and subjected to RT-PCR analysis to determine the mRNA levels of IL-20.

Results obtained from this experiment show that OxLDL induced IL-20 expression in human peripheral monocytes and mouse RAW264.7 macrophages.

OxLDL has been shown to promote foam cell development and other comprising endothelial functions by triggering the secretion of chemokines and increasing the expression of leukocyte adhesion molecules. See Seinberg et al., *Nat Med.*, 8:1211-1217, 2002. Thus, the above-described results explain the co-localization of foam cells and IL-20 determined by immunohistochemical staining.

I1-20 was also found to be induced under hypoxic conditions. It is known that hypoxia induces various angiogenesis factors, resulting in neovascularization in ischemic tissues.

Human peripheral monocytes were treated with $CoCl_2$, a factor that elicits hypoxia-like responses by activating hypoxia-inducible factor-1 α in vitro. See Yuan et al., *J. Biol. Chem.*, 278:15911-15916, 2003; and Semenza et al., *Annu. Rev. Cell Dev. Biol.*, 15:551-578, 1999. Briefly, human peripheral monocytes ($1 \times 10^6$) were isolated and incubated with 100 µM or 500 µM of $CoCl_2$ for 6 hours. Human umbilical vein endothelial cells (HUVECs) were incubated with serum-free M199 and treated with $CoCl_2$ for 6 hours at the same concentration or incubated with 1% $O_2$ and 5% $CO_2$ for 12 hours.

Results of RT-PCR indicate that IL-20 was induced in $CoCl_2$ treated human peripheral monocytes. $CoCl_2$ upregulates the expression of IL-20, IL-20R1, and IL-20R2, but not IL-22R1 in human umbilical vein endothelial cells (HUVECs). Similar results were obtained in HUVECs incubated in a chamber supplied with 1% $O_2$ to minic a hypoxia condition for 12 hours.

Taken together, hypoxia was found to induce the expression of both IL-20 and its receptors.

IL-20 Induces Chemokines and Promotes Angiogenesis

The progression of atherosclerosis involves recruitment of T lymphocytes to atherosclerotic lesions. Three CXCR3 ligands, Mig/CXCL9, IP-10/CXCL10, and I-TAC/CXCL11, mediate this T lymphocyte recruitment process and are found to be associated with atheroma. Mach et al., *J. clin. Invest.*, 104:1041-1050, 1999.

The effect of IL-20 on the levels of these chemokines was investigated. HUVEC cells were cultured in media containing IL-20 and the levels of these CXCR3 ligands were examined by RT-PCR. Results indicate that CXCL9 and CXC11, but not CXCL 10, are upregulated by IL-20 in HUVECs and in human microvessel endothelial cells.

The effect of IL-20 on angiogenesis was also investigated. Balb/c mice were subcutaneously injected with mouse hepatoma cells, ML-1 ($1 \times 10^6$), together with Matrigel containing mIL-20, mIL-20 and anti-mIL-20R1 antibody, or VEGF. Seven days later, tumors were excised and stained with CD31 for microvessel density analysis. Similar to VEFG, mIL-20 enhanced vascularization around the solid tumors compared to saline-treated controls. CD31 staining also showed higher microvessel density in tumors excised from mIL-20 treated mice than that in saline-treaded mice. In addition, antibody against mouse IL-20R1 inhibited mIL-20 induced angiogenesis, indicating that IL-20R1 was involved in IL-20 induced angiogenesis.

As angiogenesis is critical to the development of tumor, especially solid tumor, agents that inhibit IL-20 induced angiogenesis, e.g., anti-IL-20 antibody, can be used to treat tumor.

IL-20 Promotes Atherosclerosis in Apolipoprotein E-deficient Mice

Full length mIL-20 cDNA was amplified by PCR, using the following primers:

```
Sense primer:
5'- ATGAAAGGCTTTGGTCTTGA -3'      (SEQ ID NO: 7)

Antisense primer:
5'- TAGCATCTCCTCCATCCATCT -3'     (SEQ ID NO: 8)
```

The amplified cDNA, with a hexa-histidine tag, was inserted into pcDNA3.1 to construct an mIL-20 expression vector.

Fifty micrograms of the mIL-20 expression vector was delivered to 14-week old female ApoE$^{-/-}$ mice by intramuscular injection at the bilateral quadriceps muscle. Immediately after injection, transcutaneous electric pulses were applied as described in Chen et al., *Genes Immun.*, 6:493-499, 2005. The electroporation was performed on muscles of alternate tibias of each mouse once a week for 10 weeks. These mice were fed with atherogenic diet during this period of time. They were then sacrificed and their atherosclerotic lesion areas analyzed.

The serum IL-20 levels after eletroporation were measured using ELISA. Results show that the IL-20 protein levels peaked at the first week after electroporation and gradually reduced in the following weeks. Administration of IL-20 led to enhanced en face lesions of aortas, aortic sinus. Numbers of Mac-3 positive macrophages were also increased at the aortic sinus. The expression of Mig and I-TAC were also increased in aortas of mice treated with mIL-20 compared to control mice. Further, proinflammatory cytokines, e.g., tumor necrosis factor-α and IL-6, were also upregulated in the aortas of mice treated with mIL-20. These results suggest that IL-20 is a proatherogenic factor and may contribute to the pathogenesis of atherosclerosis.

Upregulation of both IL-20 and its Receptors in Synovial Fluid of RA Patients

Sixteen rheumatoid arthritis (RA) patients, 32 osteoarthritis (OA) patients, 8 gout patients, and 10 healthy volunteers were participated in this study.

All of the RA patients (10 females and 6 males, aged 34-87) showed radiographic features of uniform joint space narrowing and were rheumatoid factor positive. In addition, all of them met 4 out of the seven criteria for RA established by the American College of Rheumatology. See Arnett, et al., *Arthritis Rheum.*, 31:315-324, 1988.

The OA patients (21 females and 11 males, aged 48-82) displayed radiographic features including non-uniform joint space narrowing, subchondral sclerosis, subchondral cysts, and osteohyte formation. The gout patients (1 female and 7 males, aged 47-83) were diagnosed based on the presence of uric acid crystal deposits in their joint fluids.

Synovial fluid samples were collected from keen joints of all of the participants using needle aspiration. Blood samples were also collected from these participants. Fresh synovial fluid, synovial tissue, and blood samples were prepared according to standard procedures. Briefly, synovial fluid was digested with hyaluronidase and applied to a nylon-mesh column (100-mm pore size). The flow-through was collected and added to an equal volume of Histopaque, centrifuged (1,800 rpm for 30 minutes at room temperature), and the supernatant was collected. Synovial tissues were rinsed twice with phosphate buffered saline, stored overnight in 3.7% formaldehyde, and then dehydrated (in formalin, alcohol, and xylene series) and embedded in paraffin (5-mm paraffin blocks on silane-coated slides). Blood was centrifuged (2,000 rpm for 10 minutes) and sera were collected. All samples were stored at −80° C. until being used.

Enzyme-linked immunosorbent assay (ELISA) was performed to determine the IL-20 levels in synovial fluid and serum, using a human IL-20 monoclonal antibody. See Wei et al., *Clin. Immunol.*, 117:65-72, 2005.

The IL-20 concentration in synovial fluid of the RA patients was significantly higher than that of the OA patients (p<0.0001) and gout patients (p<0.05). Median levels of IL-20 in synovial fluid from the RA, OA, and gout patients were 432.1 ng/ml ($25^{th}$ to $75^{th}$ percentiles 25.4-1,653 ng/ml), 0 ng/ml ($25^{th}$ to $75^{th}$ percentiles 0-8.5 ng/ml), and 0 ng/ml ($25^{th}$ to $75^{th}$ percentiles 0-26.7 ng/ml), respectively.

IL-20 levels in sera of 12 RA patients and 10 healthy volunteers were determined following the method described above. Serum IL-20 levels of IL-20 in the RA patients were very similar to that in the healthy controls (P=0.3544). Median levels of IL-20 in serum from RA patients and healthy controls were 99.5 ng/ml ($25^{th}$ to $75^{th}$ percentiles 96.5-102.5 ng/ml) and 98.5 ng/ml ($25^{th}$ to $75^{th}$ percentiles 90.5-102.5 ng/ml), respectively.

These data suggest that the high level of IL-20 in the synovial fluid of RA patients is produced locally.

Expression of IL-20 and Its Receptors in RA Synovial Membranes and RA Synovial Fibroblasts Immunohistochemical staining was performed to examine the expression of IL-20 and its receptors in RA synovial membranes. Briefly, the synovial tissues were prepared as described above. The paraffin on the synovial membranes was removed using xylene, and the membranes were rehydrated using ethanol. The slides were treated with blocking agents, which can reduce background staining (DakoCttomation, Carpinteria, Calif.) and then incubated with monoclonal antibodies specific to IL-20, IL-20RI (both from R&D Systems, Minneapolis, Minn.) and IL-20RII in the blocking agents. The slides were then treated consecutively with the secondary antibody, horseradish peroxidase-conjugated goat anti-mouse IgG (Chemicon, Temecula, Calif.), and diaminobenzidine substrates (Vector, Burlingame, Calif.). After incubation, the slides were washed and counterstained with Nayer's hematoxylin (Thermo Shandon, Pittburgh, Pa.). Mouse IgG1 isotype (clone 11711; R&D Systems) was used as a negative control.

Most of the synovial membrane cells in the intimal lining layer showed strong positive immunoreactivity, while cells in the sublining layer showed moderate positive immunoreactivity. Negative controls using mouse IgG1 isotype antibody showed no detectable immunoreactivity. These results indicate that IL-20 and its receptors IL-20RI and IL-20RII are all expressed in RA synovial membranes.

The expression of IL-20 and its receptors was also examined in RA synovial fibroblasts (RASFs). Freshly isolated synovial tissue obtained from RA patients was finely minced into 2-3mm pieces and subjected to Dispase (Roche, Mannheim, Germany) digestion in Dulbecco's modified Eagle's medium (DEME, Gibco BRL, Grand Island, NY) for 1 hour at 37° C. RASFs were cultured in DEME containing 10% fetal bovine serum. All in vitro experiments were performed using primary cultures of the RASFs between passages 5 and 12. The RASFs were cultured on sterile glass slides and then fixed in 3.7% paraformaldehyde, permeabilized using PBS with 0.1% Triton X-100. Nonspecific binding sites were blocked by incubating the RASFs in PBS with 0.1% bovine serum albumin (weight/volume). The presence of IL-20, IL-20RI and IL-20RII proteins were then detected by immunostaining as described above.

Cells isolated from RA synovial membranes (RASFs) were found to express IL-20 and its receptors. Their expression patterns are similar to those found in immuno-staining of RA synovial membranes. It was also found that IL-20 induces expression of phosphorylated ERK-½ in a time-dependent manner. No significant changes of levels of phorphorylated p38, MAPK or JNK were observed in RASFs treated with IL-20.

IL-20 Induces Neutrophil Chemotaxis and RASF Migration in vitro

Neutrophil chemotaxis was analyzed using a 48-well chamber (modified Boyden chamber) housing a polycarbonate filter with 8 μM pores (Nucleopore, Cabin John, Md.). The upper wells were loaded with $5 \times 10^4$ neutrophils. The lower chambers were filled with human IL-20 (200 ng/ml) or phorbol myristate acetate (PMA) (20 ng/ml), in RPMI 1640 medium containing 0.2% FBS. RPMI 1640 with 0.2% FBS was used as a negative control, and PMA as a positive control. The chambers were incubated for 1 hour at 37° C. Cells adhering to the lower side of the filter were fixed in methanol and stained in a Giemsa solution for cell counting. The number of neutrophils on the lower surface of the filter was determined microscopically by counting 12 randomly selected fields at 200× magnification.

T cell migration was analyzed following the method described above, except that a polycarbonate filter with 5-μM pores was used.

To investigate RASF migration, the upper wells were loaded with 6,500 RASFs and a polycarbonate filter with 8-mM pores were used. The lower chambers were filled with human IL-20 (200 ng/ml) or transforming growth factor β1 (TGFβ1)(50 ng/ml) as a positive control, in DMEM containing 0.2% FBS. The chambers were incubated for 4.5 hours at 37° C. The number of RASFs was determined microscopically at 100× magnification.

IL-20 induced significantly greater neutrophil chemotaxis and RASF migration than negative controls ($P < 0.01$). It, however, did not induce T cell migration. Chemotaxis of neutrophils and RASF migration are known to be important in the pathogenesis of RA. These data thus suggest that IL-20 is involved in RA development.

Statistical comparisons of each treated group with control groups with regard to these migration data were performed with one-way analysis of variance (ANOVA), using Dunnett's procedure for multiple comparisons.

IL-20 Receptor I Prevents Collagen-induced Arthritis

Eight-week old male Sprague-Dawley rats were immunized with an emulsion containing equal parts of Freund's complete adjuvant, 4 mg/ml of heat-killed mycobacterium tuberculosis and bovine type II collagen solubilized at 2 mg/ml in 0.05M acetic acid. Each rat was injected intradermally in its dorsum with 200 μl of the emulsion. It also received booster doses on day 7 subcutaneously in the base of its tail with 100 ml of the same emulsion.

The severity of arthritis in each hind paw was monitored and scored on a scale of 0-5, where:

0: no redness or swelling;

1: slight swelling in rat's-ankle or redness in its foot;

2: progressive swelling, inflammation, and redness from the ankle to the midfoot;

3: swelling and inflammation of the entire foot, not including toes;

4: swelling and inflammation of the entire foot, including toes;

5: swelling and inflammation of the entire foot with loss of mobility.

A score $\geq 3$ represents severe swelling. The severity of arthritis in each rat was determined independently and blindly by four individual observers, and the average of their scores were calculated.

Soluble forms (extracellular domains) of rat IL-20 receptors IL-20RI and IL-20RII (sIL-20RI and sIL-20RII) were fused with a histidine tag at their 3' end and cloned into pcDNA3.1 expression vector. The plasmid DNAs were delivered into testing rats as follows. Two hundred fifty micrograms of plasmid DNAs carrying either sIL-20RI or sIL-20RII were injected into their bilateral quadriceps muscles, and transcutaneous electric pulses were administered immediately thereafter as described above. Five pulses of 200 volts were administered at each injection site at a rate of 1 pulse/second and a duration of 75 msec for each pulse. Electrode paste was used to prevent skin burns.

Two days after the initial immunization with CII, the rats were divided On day 5 and 10 after initial injections of bovine CII, the testing rats were divided into 5 groups, each subjected to electroporation on days 5 and 10 with sIL-20RI, sIL-20RII, pcDNA 3.1, PBS, and CII. The effect of in vivo intramuscular administration of soluble IL-20 receptors on the severity of CLL induced arthritis was evaluated from day 12 to day 20. The severity of arthritis in each hind paw was evaluated visually and scored as described above. Arthritis severity scores on day 20 were significantly lowered in rats injected with sIL-20RI compared with that in rats injected with plasmid control ($p < 0.01$). The median severity scores were 4.3 ($25^{th}$ to $75^{th}$ percentiles 4-4.4) for the collagen control, 4.1 ($25^{th}$ to $75^{th}$ percentiles 3.8-4.3) for the PBS control, and 3.5 ($25^{th\ to}\ 75^{th\ percentiles}$ 3.3-4.4) for the plasmid control. The median stores for rats treated with soluble IL-20 receptors were much lower, i.e., 0.6 ($25^{th}$ to $75^{th}$ percentiles 0-2.1) for rats treated with sIL-20RI and 3.4 ($25^{th}$ to $75^{th}$ percentiles 1.1-4.3) for rats treated with sIL-20RII. These results demonstrate that sIL-20RI significantly reduced the severity of collagen-induced-arthritis. As soluble IL-20 receptors are known to block IL-20/IL-20 receptor signaling pathway, these data suggest that IL-20 signaling plays an important role in collagen induced arthritis. Accordingly, agents that can inhibit this pathway, e.g., anti-IL-20 antibodies, might be effective in treating this disease.

Statistical analysis using GraphPad Prism 4.0 software was performed to all of the obtained data. The Kiruska-Wallis test was used to compare synovial fluid IL-20 levels and arthritis severity scores between different groups. Post hoc comparisons were performed with Dunn's multiple comparison test. The difference between treated and control groups regarding severity swelling (defined as a severity score $\geq 3$) in hind paws of these animals was statistically significant.

Generation of Anti-IL-20 Monoclonal Antibody 7E

BALB/cJ mice were immunized subcutaneously once a week for 4 weeks with recombinant hIL-20 protein (100 μg/mouse) emulsified with an equal volume of Freund's complete/incomplete adjuvant. Three days before cell fusion, three mice were boosted with the antigen free from adjuvant by intravenous injection. Spleen cells ($1.2 \times 10^8$) from the immunized mice were fused with X63-Ag8-6.5.3 myeloma cells ($1.5 \times 10^7$) with PEG 4000 (Merck & Co., Inc., Whitehouse Station, N.J.). The fused cells were distributed into 24-well plates and cultured in HAT medium for 14 days. Culture supernatant was examined for antibody reacting with hIL-20 by ELISA. Limited dilution was performed to fused cells that produce antibodies reacting to hIL-20. The hybridoma cells were cultured in Dulbecco's Modified Eagle's medium (GIBCO; Invitrogen Corporation, Carlsbad, Calif.)

containing 15% fetal calf serum, 1% penicillin/streptomycin, 2% L-glutamine, and 1% adjusted $NaHCO_3$ solution. The isotype of the selected antibody, IgG, was determined using isotyping ELISA. The antibody was purified from ascites using Protein-A chromatography. The hybridoma producing anti hIL-20 monoclonal antibody 7E (mAb 7E) is deposited on Oct. 16, 2007 at the American Type Culture Collection, 10801 University Boulevard, Manassas, Va. 20110-2209, U.S.A. and has been assigned a deposit number PTA-8687. This antibody was found to specifically recognize human IL-20 by western-blot analysis.

Genes encoding the heavy and light chains of mAb 7E were cloned as follows. Total RNA was isolated from the hybridoma cells and then treated with calf intestinal phosphatase (CIP) to remove the 5' phosphates. The dephosphorylated RNA was treated with tobacco acid pyrophosphatase (TAP) to remove the 5' cap structure from intact, full-length mRNA followed by ligating to the GeneRacer™ RNA Oligo (5'-CGACUGGAGCACGAGGACACUGACAUG-GACUGAAGGAGUAGAAA-3') (SEQ ID NO:9) (GeneRacer kit, Invitrogen) at the 5' end of the mRNA using T4 RNA ligase.

The ligated mRNA was reverse transcribed using SuperScript™ III reverse transcriptase and the GeneRacer™ Oligo dT Primer (5'-GCTGTCAACGATACGCTACGTAACG GCATGACAGTGTTTTTTTTTTTTTTTTTTTTTTTT-3') (SEQ ID NO:10) to generate the RACE-ready first-strand cDNA with known priming sites at the 5' and 3' ends. To obtain the 5' ends of cDNA, PCR was performed on the first-strand cDNA template using sequences of constant region of antibody as a reverse gene-specific primer (For heavy chain: 5'-CTGCTGGCCGGGTGGGCAACGT-3' (SEQ ID NO:11); for light chain: 5'-GTGAGTGGCCTCA-CAGGTATAGCT-3') (SEQ ID NO:12) and the GeneRacerTm 5' Primer (5'-CGACTGGAGCACGAGGACACTGA-3') (SEQ ID NO:13). Only mRNA that has the GeneRacer™ RNA Oligo ligated to the 5' end was completely reverse transcribed and amplified using PCR. Additional PCR was performed with the GeneRacer™ 5' nested primer (5'-GGA-CACTGACATGGACTGAAGGAGTA-3') (SEQ ID NO:14) and gene-specific nested primer (For heavy chain: 5'-AC-CGCTGGACAGGGATCCAGAGTT-3' (SEQ ID NO:15); for light chain: 5'-GAGGGTGCTGCTCATGCTGTAGGT-3' (SEQ ID NO:19) to identify specific PCR products.

To obtain 3' ends, the first-strand cDNA was amplified using a forward gene-specific primer (For heavy chain: 5'-CATGAGGGCCTGCACAACCACCAT-3' (SEQ ID NO:16); for light chain: 5'-CCCACCATCCAGTGAG-CAGTTAACA-3') (SEQ ID NO: 17) and the GeneRacerTm 3' Primer (5'-GCTGTCAACGATACGCTACGTAACG-3') (SEQ ID NO: 18). Only mRNA that has a polyA tail was reverse transcribed and amplified by PCR. All the PCR products were gel-purified and subcloned into pCR4-TOPO vector for sequencing. According to the nucleotide sequences obtained from 5' and 3' RACE, specific primers for heavy and light chains were designed to amplify the full-length cDNA from RACE-ready cDNA template for antibody expression in mammalian cells.

Monoclonal Antibody 7E Inhibits IL-20 Induced Proliferation of Calf Pulmonary Artery Endothelial Cells (CPAEs) and Human HUVEC mAb 7E was found to neutralize the proliferation of CPAE cells and HUVEC cells induced by IL-20.

CPAEs were plated in 24-well plates at a density of $1 \times 10^4$ cells per well. After 24 hours of incubation in normal growth medium, cells were exposed to various concentrations of hIL-20 for 72 hours. Cells were then incubated with a 1-mg/ml solution of 3-[4,5-Dimethylthiazol-2-yl]-2,5-diphenyltetrazolium bromide (MTT) (Sigma, St. Louis, Mo.) for 4 hours. Two hundred pl of DMSO (Dimethyl Sulfoxide) (Sigma) was added to the culture. Absorbance of 550 nm was determined using an ELISA reader. The absorbance of cytokine-treated cells was expressed as a percentage of untreated control cells. Basic fibroblast growth factor (bFGF) (Sigma) was used as the positive control in the cell proliferation assay.

Human IL-20W, a splicing variant of human IL-20, induced CPAE proliferation at a concentration of 25-1000 ng/ml. Human IL-20S, another splicing variant of human IL-20, also induced CPAE proliferation, but at a much lower concentration, i.e., 12-100 ng/ml. Interestingly, a high concentration of IL-20 (>1000 ng/ml of IL-20W and >200 ng/ml of IL-20S) inhibited CPAE proliferation.

The effect of monoclonal antibody 7E on IL-20 induced cell proliferation was examined as follows. CPAEs were seeded at a density of $1 \times 10^4$ cells per well in 24-well plates for 24 hours at 37° C. Before treatment, 10-folds excess of anti-hIL-20 monoclonal antibody 7E or sIL-20R1 or sIL-20R2 protein were incubated with an optimal concentration of hIL-20S (100 ng/ml) or hIL-20W (250 ng/ml) for 30 minutes at 4° C. The mixtures of IL-20 with 7E or IL-20 with sIL-20R1 or IL-20 with sIL-20R2 were added to the CPAEs and incubated for 72 hours. Cells were then incubated with 1 mg/ml MTT solution for 4 hours. Two hundred μl of DMSO was added to the culture. Absorbance of 550 nm was determined using an ELISA reader.

Similar to the soluble receptors of IL-20, Antibody 7E blocked IL-20W induced CPAE proliferation significantly. It also blocked IL-20S induced cell proliferation, but less significantly.

The effect of Antibody 7E on IL-20 induced HUVEC proliferation was also investigated following the method described above and similar results were revealed.

These results demonstrate that monoclonal antibody 7E inhibits the activity of human IL-20.

Treating Collagen-induced Arthritis with Monoclonal Antibody 7E

Rats having collagen-induced arthritis (CIA) is a well-developed animal model for studying human rheumatoid arthritis. This model is thus employed to examine the efficacy of monoclonal antibody 7E for treating RA.

Male Sprague-Dawley rats were divided into four groups (5 rats in each group): 1. vehicle control group, in which rats were treated with collagen II (CII) and PBS; 2. Enbrel group, in which rats were treated with CII and Enbrel [3 mg/kg subcutaneously]; 3. antibody 7E group, in which rats were treated with CII and 7E [3 mg/kg subcutaneously]; 4. healthy control group. All of the rats were first immunized with collagen II to induce CIA. The thickness of the hind paws in all rats was significantly and consistently increased from day 11 after immunization. Rats of groups 1-3 were then injected with Enbrel, 7E or PBS once every two days for four times (on days 11, 13, 15, and 17). Group 4 rats were used as healthy controls.

The severity of arthritis after drug treatment was measured and compared with the healthy controls. During the course of treatment, no significant difference in body weight was observed before and after treatment ($P>0.05$), indicating that 7E has no significant impact on the systemic physical condition of the rats with CIA. The effect of 7E in CIA rats was evaluated from day 11 until day 25. The swelling of each hind paw was measured in millimeters by a vernier caliper. The swelling of the hind paws was significantly suppressed after 7E or Enbrel treatment, when compared with the vehicle controls ($P<0.05$). The thicknesses of the hind paws on day 18 were also significantly lower in rats treated with 7E than in PBS control rats ($P<0.05$). The median values of hind paws thickness of vehicle controls and healthy controls were 1.05 ($25^{th}$ to $75^{th}$ percentiles 1.01.11) and 0.52 ($25^{th}$ to $75^{th}$ percentiles 0.52-0.53), respectively. Those of rats treated with 7E and Enbrel were 0.85 ($25^{th}$ to $75^{th}$ percentiles 0.71-0.95) and 0.86 ($25^{th}$ to $75^{th}$ percentiles 0.76-0.91), respectively. These results clearly demonstrate that monoclonal antibody 7E reduced the severity of CIA as efficiently as Enbrel, a commercial drug for treating RA and other inflammatory diseases. Thus, the IL-20 monoclonal antibody, 7E, can be used as a drug to treat rheumatoid arthritis or other inflammatory disease as Enbrel, e.g., psoriasis, psoriatic arthritis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An antibody specifically binding to human IL-20, wherein the antibody contains a $V_H$ region including all the complementarity-determining regions in the $V_H$ region of mAb 7E and a $V_L$ region including all the complementarity-determining regions in the $V_L$ region of mAb 7E, and wherein mAb 7E is produced by the hybridoma cell line deposited with the American Type Culture Collection as Deposit Number PTA-8687.

2. The antibody of claim 1, wherein the antibody contains the $V_H$ and $V_L$ regions of mAb 7E.

3. The antibody of claim 2, wherein the antibody is Fab, $F(ab')_2$, scFv, or a chimeric antibody of mAb 7E.

4. The antibody of claim 1, wherein the antibody is a humanized antibody.

* * * * *

SEQUENCE LISTING

```
<160> NUMBER OF SEQ ID NOS: 21

<210> SEQ ID NO 1
<211> LENGTH: 1395
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(1392)

<400> SEQUENCE: 1 atg tac ttg gga ctg aac tat gta ttc ata gtt ttt ctc tta aat ggt        48
Met Tyr Leu Gly Leu Asn Tyr Val Phe Ile Val Phe Leu Leu Asn Gly
 1               5                  10                  15 gtc cag agt gaa ttg aag ctt gag gag tct gga gga ggc ttg gtg cag        96
Val Gln Ser Glu Leu Lys Leu Glu Glu Ser Gly Gly Gly Leu Val Gln
            20                  25                  30 cct gga gga tcc atg aaa ctc tct tgt gct gcc tct gga ttc act ttt       144
Pro Gly Gly Ser Met Lys Leu Ser Cys Ala Ala Ser Gly Phe Thr Phe
        35                  40                  45 agt gac gcc tgg atg gac tgg gtc cgc cag tct cca gag aag ggg ctt       192
Ser Asp Ala Trp Met Asp Trp Val Arg Gln Ser Pro Glu Lys Gly Leu
    50                  55                  60 gag tgg att gct gaa att aga agc aaa gct aat aat tat gca aca tac       240
Glu Trp Ile Ala Glu Ile Arg Ser Lys Ala Asn Asn Tyr Ala Thr Tyr
65                  70                  75                  80 ttt gct gag tct gtg aaa ggg agg ttc acc atc tca aga gat gat tcc       288
Phe Ala Glu Ser Val Lys Gly Arg Phe Thr Ile Ser Arg Asp Asp Ser
                85                  90                  95 aaa agt ggt gtc tac ctg caa atg aac aac tta aga gct gag gac act       336
Lys Ser Gly Val Tyr Leu Gln Met Asn Asn Leu Arg Ala Glu Asp Thr
            100                 105                 110 ggc att tat ttc tgt acc aag tta tca cta cgt tac tgg ttc ttc gat       384
Gly Ile Tyr Phe Cys Thr Lys Leu Ser Leu Arg Tyr Trp Phe Phe Asp
        115                 120                 125 gtc tgg ggc gca ggg acc acg gtc acc gtc tcc tca gcc aaa acg aca       432
Val Trp Gly Ala Gly Thr Thr Val Thr Val Ser Ser Ala Lys Thr Thr
    130                 135                 140 ccc cca tct gtc tat cca ctg gcc cct gga tct gct gcc caa act aac       480
Pro Pro Ser Val Tyr Pro Leu Ala Pro Gly Ser Ala Ala Gln Thr Asn
145                 150                 155                 160
```

```
tcc atg gtg acc ctg gga tgc ctg gtc aag ggc tat ttc cct gag cca        528
Ser Met Val Thr Leu Gly Cys Leu Val Lys Gly Tyr Phe Pro Glu Pro
            165                 170                 175 gtg aca gtg acc tgg aac tct gga tcc ctg tcc agc ggt gtg cac acc        576
Val Thr Val Thr Trp Asn Ser Gly Ser Leu Ser Ser Gly Val His Thr
        180                 185                 190 ttc cca gct gtc ctg cag tct gac ctc tac act ctg agc agc tca gtg        624
Phe Pro Ala Val Leu Gln Ser Asp Leu Tyr Thr Leu Ser Ser Ser Val
    195                 200                 205 act gtc ccc tcc agc acc tgg ccc agc gag acc gtc acc tgc aac gtt        672
Thr Val Pro Ser Ser Thr Trp Pro Ser Glu Thr Val Thr Cys Asn Val
210                 215                 220 gcc cac ccg gcc agc agc acc aag gtg gac aag aaa att gtg ccc agg        720
Ala His Pro Ala Ser Ser Thr Lys Val Asp Lys Lys Ile Val Pro Arg
225                 230                 235                 240 gat tgt ggt tgt aag cct tgc ata tgt aca gtc cca gaa gta tca tct        768
Asp Cys Gly Cys Lys Pro Cys Ile Cys Thr Val Pro Glu Val Ser Ser
                245                 250                 255 gtc ttc atc ttc ccc cca aag ccc aag gat gtg ctc acc att act ctg        816
Val Phe Ile Phe Pro Pro Lys Pro Lys Asp Val Leu Thr Ile Thr Leu
            260                 265                 270 act cct aag gtc acg tgt gtt gtg gta gac atc agc aag gat gat ccc        864
Thr Pro Lys Val Thr Cys Val Val Val Asp Ile Ser Lys Asp Asp Pro
        275                 280                 285 gag gtc cag ttc agc tgg ttt gta gat gat gtg gag gtg cac aca gct        912
Glu Val Gln Phe Ser Trp Phe Val Asp Asp Val Glu Val His Thr Ala
    290                 295                 300 cag acg caa ccc cgg gag gag cag ttc aac agc act ttc cgc tca gtc        960
Gln Thr Gln Pro Arg Glu Glu Gln Phe Asn Ser Thr Phe Arg Ser Val
305                 310                 315                 320 agt gaa ctt ccc atc atg cac cag gac tgg ctc aat ggc aag gag ttc       1008
Ser Glu Leu Pro Ile Met His Gln Asp Trp Leu Asn Gly Lys Glu Phe
                325                 330                 335 aaa tgc agg gtc aac agt gca gct ttc cct gcc ccc atc gag aaa acc       1056
Lys Cys Arg Val Asn Ser Ala Ala Phe Pro Ala Pro Ile Glu Lys Thr
            340                 345                 350 atc tcc aaa acc aaa ggc aga ccg aag gct cca cag gtg tac acc att       1104
Ile Ser Lys Thr Lys Gly Arg Pro Lys Ala Pro Gln Val Tyr Thr Ile
        355                 360                 365 cca cct ccc aag gag cag atg gcc aag gat aaa gtc agt ctg acc tgc       1152
Pro Pro Pro Lys Glu Gln Met Ala Lys Asp Lys Val Ser Leu Thr Cys
    370                 375                 380 atg ata aca gac ttc ttc cct gaa gac att act gtg gag tgg cag tgg       1200
Met Ile Thr Asp Phe Phe Pro Glu Asp Ile Thr Val Glu Trp Gln Trp
385                 390                 395                 400 aat ggg cag cca gcg gag aac tac aag aac act cag ccc atc atg gac       1248
Asn Gly Gln Pro Ala Glu Asn Tyr Lys Asn Thr Gln Pro Ile Met Asp
                405                 410                 415 aca gat ggc tct tac ttc gtc tac agc aag ctc aat gtg cag aag agc       1296
Thr Asp Gly Ser Tyr Phe Val Tyr Ser Lys Leu Asn Val Gln Lys Ser
            420                 425                 430 aac tgg gag gca gga aat act ttc acc tgc tct gtg tta cat gag ggc       1344
Asn Trp Glu Ala Gly Asn Thr Phe Thr Cys Ser Val Leu His Glu Gly
        435                 440                 445 ctg cac aac cac cat act gag aag agc ctc tcc cac tct cct ggt aaa       1392
Leu His Asn His His Thr Glu Lys Ser Leu Ser His Ser Pro Gly Lys
    450                 455                 460 tga                                                                   1395
```

```
<210> SEQ ID NO 2
<211> LENGTH: 464
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Met Tyr Leu Gly Leu Asn Tyr Val Phe Ile Val Phe Leu Leu Asn Gly
 1               5                  10                  15

Val Gln Ser Glu Leu Lys Leu Glu Glu Ser Gly Gly Gly Leu Val Gln
             20                  25                  30

Pro Gly Gly Ser Met Lys Leu Ser Cys Ala Ala Ser Gly Phe Thr Phe
         35                  40                  45

Ser Asp Ala Trp Met Asp Trp Val Arg Gln Ser Pro Glu Lys Gly Leu
     50                  55                  60

Glu Trp Ile Ala Glu Ile Arg Ser Lys Ala Asn Asn Tyr Ala Thr Tyr
 65                  70                  75                  80

Phe Ala Glu Ser Val Lys Gly Arg Phe Thr Ile Ser Arg Asp Asp Ser
                 85                  90                  95

Lys Ser Gly Val Tyr Leu Gln Met Asn Asn Leu Arg Ala Glu Asp Thr
            100                 105                 110

Gly Ile Tyr Phe Cys Thr Lys Leu Ser Leu Arg Tyr Trp Phe Phe Asp
        115                 120                 125

Val Trp Gly Ala Gly Thr Thr Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365
```

```
Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460
```

<210> SEQ ID NO 3
<211> LENGTH: 363
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(363)

<400> SEQUENCE: 3

```
gaa ttg aag ctt gag gag tct gga gga ggc ttg gtg cag cct gga gga       48
Glu Leu Lys Leu Glu Glu Ser Gly Gly Gly Leu Val Gln Pro Gly Gly
  1               5                  10                  15 tcc atg aaa ctc tct tgt gct gcc tct gga ttc act ttt agt gac gcc       96
Ser Met Lys Leu Ser Cys Ala Ala Ser Gly Phe Thr Phe Ser Asp Ala
             20                  25                  30 tgg atg gac tgg gtc cgc cag tct cca gag aag ggg ctt gag tgg att      144
Trp Met Asp Trp Val Arg Gln Ser Pro Glu Lys Gly Leu Glu Trp Ile
         35                  40                  45 gct gaa att aga agc aaa gct aat aat tat gca aca tac ttt gct gag      192
Ala Glu Ile Arg Ser Lys Ala Asn Asn Tyr Ala Thr Tyr Phe Ala Glu
     50                  55                  60 tct gtg aaa ggg agg ttc acc atc tca aga gat gat tcc aaa agt ggt      240
Ser Val Lys Gly Arg Phe Thr Ile Ser Arg Asp Asp Ser Lys Ser Gly
 65                  70                  75                  80 gtc tac ctg caa atg aac aac tta aga gct gag gac act ggc att tat      288
Val Tyr Leu Gln Met Asn Asn Leu Arg Ala Glu Asp Thr Gly Ile Tyr
                 85                  90                  95 ttc tgt acc aag tta tca cta cgt tac tgg ttc ttc gat gtc tgg ggc      336
Phe Cys Thr Lys Leu Ser Leu Arg Tyr Trp Phe Phe Asp Val Trp Gly
            100                 105                 110 gca ggg acc acg gtc acc gtc tcc tca                                  363
Ala Gly Thr Thr Val Thr Val Ser Ser
        115                 120
```

<210> SEQ ID NO 4
<211> LENGTH: 720
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(717)

<400> SEQUENCE: 4

```
atg atg agt cct gcc cag ttc ctg ttt ctg tta gtg ctc tgg att cgg      48
Met Met Ser Pro Ala Gln Phe Leu Phe Leu Leu Val Leu Trp Ile Arg
 1               5                  10                  15 gaa acc aac ggt gat ttt gtg atg acc cag act cca ctc act ttg tcg      96
Glu Thr Asn Gly Asp Phe Val Met Thr Gln Thr Pro Leu Thr Leu Ser
                20                  25                  30 gtt acc att gga caa cca gcc tcc atc tct tgc aag tca agt cag agc     144
Val Thr Ile Gly Gln Pro Ala Ser Ile Ser Cys Lys Ser Ser Gln Ser
            35                  40                  45 ctc ttg gat agt gat gga aag aca tat ttg aat tgg ttg tta cag agg     192
Leu Leu Asp Ser Asp Gly Lys Thr Tyr Leu Asn Trp Leu Leu Gln Arg
 50                  55                  60 cca ggc cag tct cca aag cac ctc atc tat ctg gtg tct aaa ctg gac     240
Pro Gly Gln Ser Pro Lys His Leu Ile Tyr Leu Val Ser Lys Leu Asp
65                  70                  75                  80 tct gga gtc cct gac agg ttc act ggc agt gga tcg ggg acc gat ttc     288
Ser Gly Val Pro Asp Arg Phe Thr Gly Ser Gly Ser Gly Thr Asp Phe
                85                  90                  95 aca ctg aga atc agc aga gtg gag gct gag gat ttg gga gtt tat tat     336
Thr Leu Arg Ile Ser Arg Val Glu Ala Glu Asp Leu Gly Val Tyr Tyr
            100                 105                 110 tgc tgg caa agt aca cat ttt ccg tgg acg ttc ggt gga ggc acc aag     384
Cys Trp Gln Ser Thr His Phe Pro Trp Thr Phe Gly Gly Gly Thr Lys
        115                 120                 125 ctg gaa atc aaa cgg gct gat gct gca cca act gta tcc atc ttc cca     432
Leu Glu Ile Lys Arg Ala Asp Ala Ala Pro Thr Val Ser Ile Phe Pro
130                 135                 140 cca tcc agt gag cag tta aca tct gga ggt gcc tca gtc gtg tgc ttc     480
Pro Ser Ser Glu Gln Leu Thr Ser Gly Gly Ala Ser Val Val Cys Phe
145                 150                 155                 160 ttg aac aac ttc tac aag tgg aag att gat ggc agt gaa cga caa aat     528
Leu Asn Asn Phe Tyr Lys Trp Lys Ile Asp Gly Ser Glu Arg Gln Asn
                165                 170                 175 ggc gtc ctg aac agt tgg act gat cag ccc aaa gac atc aat gtc gac     576
Gly Val Leu Asn Ser Trp Thr Asp Gln Pro Lys Asp Ile Asn Val Asp
            180                 185                 190 agc aaa gac agc acc tac agc atg agc agc acc ctc acg ttg acc aag     624
Ser Lys Asp Ser Thr Tyr Ser Met Ser Ser Thr Leu Thr Leu Thr Lys
        195                 200                 205 gac gag tat gaa cga cat aac agc tat acc tgt gag gcc act cac aag     672
Asp Glu Tyr Glu Arg His Asn Ser Tyr Thr Cys Glu Ala Thr His Lys
210                 215                 220 aca tca act tca ccc att gtc aag agc ttc aac agg aat gag tgt tag     720
Thr Ser Thr Ser Pro Ile Val Lys Ser Phe Asn Arg Asn Glu Cys
225                 230                 235

<210> SEQ ID NO 5
<211> LENGTH: 239
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Met Met Ser Pro Ala Gln Phe Leu Phe Leu Leu Val Leu Trp Ile Arg
 1               5                  10                  15

Glu Thr Asn Gly Asp Phe Val Met Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45
```

```
Leu Leu Asp Ser Asp Gly Lys Thr Tyr Leu Asn Trp Leu Leu Gln Arg
 50                  55                  60

Pro Gly Gln Ser Pro Lys His Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Arg Ile Ser Arg Val Glu Ala Glu Asp Leu Gly Val Tyr Tyr
             100                 105                 110

Cys Trp Gln Ser Thr His Phe Pro Trp Thr Phe Gly Gly Gly Thr Lys
             115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Lys Trp Lys Ile Asp Gly Ser Glu Arg Gln Asn
                165                 170                 175

Gly Val Leu Asn Ser Trp Thr Asp Gln Pro Lys Asp Ile Asn Val Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235

<210> SEQ ID NO 6
<211> LENGTH: 339
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(339)

<400> SEQUENCE: 6 gat ttt gtg atg acc cag act cca ctc act ttg tcg gtt acc att gga      48
Asp Phe Val Met Thr Gln Thr Pro Leu Thr Leu Ser Val Thr Ile Gly
 1               5                  10                  15 caa cca gcc tcc atc tct tgc aag tca agt cag agc ctc ttg gat agt      96
Gln Pro Ala Ser Ile Ser Cys Lys Ser Ser Gln Ser Leu Leu Asp Ser
             20                  25                  30 gat gga aag aca tat ttg aat tgg ttg tta cag agg cca ggc cag tct     144
Asp Gly Lys Thr Tyr Leu Asn Trp Leu Leu Gln Arg Pro Gly Gln Ser
         35                  40                  45 cca aag cac ctc atc tat ctg gtg tct aaa ctg gac tct gga gtc cct     192
Pro Lys His Leu Ile Tyr Leu Val Ser Lys Leu Asp Ser Gly Val Pro
     50                  55                  60 gac agg ttc act ggc agt gga tca ggg acc gat ttc aca ctg aga atc     240
Asp Arg Phe Thr Gly Ser Gly Ser Gly Thr Asp Phe Thr Leu Arg Ile
 65                  70                  75                  80 agc aga gtg gag gct gag gat ttg gga gtt tat tat tgc tgg caa agt     288
Ser Arg Val Glu Ala Glu Asp Leu Gly Val Tyr Tyr Cys Trp Gln Ser
                 85                  90                  95 aca cat ttt ccg tgg acg ttc ggt gga ggc acc aag ctg gaa atc aaa     336
Thr His Phe Pro Trp Thr Phe Gly Gly Gly Thr Lys Leu Glu Ile Lys
            100                 105                 110
``` cgg                                                                    339
Arg

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgaaaggct ttggtcttga                                                   20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagcatctcc tccatccatc t                                                 21

<210> SEQ ID NO 9
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cgacuggagc acgaggacac ugacauggac ugaaggagua gaaa                        44

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgtcaacg atacgctacg taacggcatg acagtgtttt ttttttttttt tttttttttt      60

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgctggccg ggtgggcaac gt                                                22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgagtggcc tcacaggtat agct                                                      24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgactggagc acgaggacac tga                                                       23

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggacactgac atggactgaa ggagta                                                    26

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
accgctggac agggatccag agtt                                                      24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
catgagggcc tgcacaacca ccat                                                      24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccaccatcc agtgagcagt taaca                                                     25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctgtcaacg atacgctacg taacg                                                     25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gagggtgctg ctcatgctgt aggt                                          24

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 20

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Phe Cys Thr Lys Leu Ser Leu Arg Tyr Trp Phe Phe Asp Val Trp Gly
            100                 105                 110

Ala Gly Thr Thr Val Thr Val Ser Ser
        115                 120

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 21

Asp Phe Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Ser
                85                  90                  95

-continued

```
Thr His Phe Pro Trp Thr Phe Gly Gly Gly Thr Lys Leu Glu Ile Lys
            100                 105                 110
Arg
```